United States Patent [19]

Lucas et al.

[11] 4,194,840

[45] Mar. 25, 1980

[54] SENSOR CONTACT

[76] Inventors: John M. Lucas, 4816 Hutchison St., Montreal; Serge Gracovetsky, 209 du Dauphine, St. Lambert, both of Quebec, Canada

[21] Appl. No.: 881,855

[22] Filed: Feb. 27, 1978

[51] Int. Cl.² .................... G01N 21/48; G01N 21/18; G01N 21/30

[52] U.S. Cl. .................................. 356/429; 250/571; 356/445

[58] Field of Search ............. 356/429, 430, 445; 250/571, 572, 562, 563

[56] References Cited

U.S. PATENT DOCUMENTS 4,019,819  4/1977  Lodzinski ............................. 356/73

*Primary Examiner*—John K. Corbin
*Assistant Examiner*—Rodney Bovernick

[57] ABSTRACT

A sensing element having a face adapted to contact the surface of a travelling web or sheet of paper, said face formed into a convex surface that substantially is in the form of a single base segment of a sphere having a radius between 35 and 10 mm. The surface of the web is pressed against the face so that the area of contact between the surface and the face has a minimum dimension of 2 mm. In the preferred application of the present invention the element is as an optical window in an optical sensing device wherein light is passed through the window in a direction and is reflected to sensors positioned on the same side of the window as the light source.

6 Claims, 1 Drawing Figure

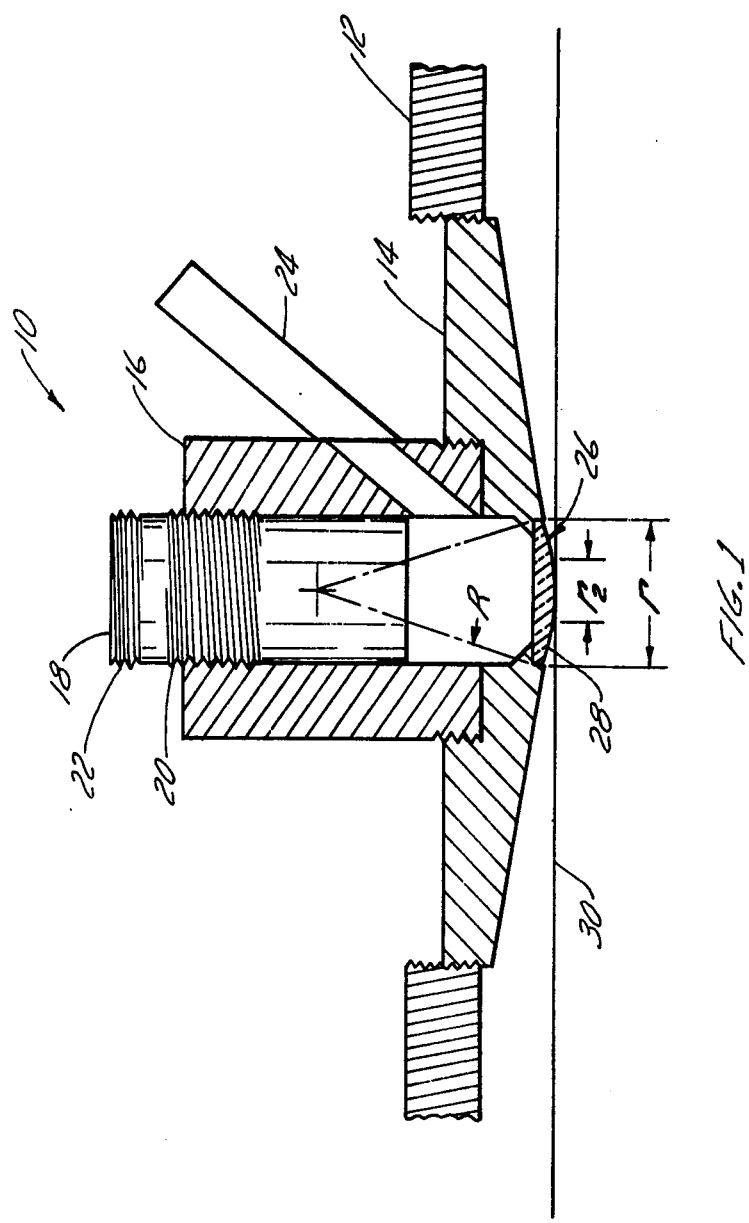

SENSOR CONTACT

FIELD OF THE INVENTION

The present invention relates to a contact element for a sensor. More particularly the present invention relates to an optical window for use in an optical sensor that is in direct contact with the travelling surface of a paper web.

DESCRIPTION OF PRIOR ART

Paper sensors for measuring characteristics of travelling webs are generally positioned in spaced relationship to the surface of the material being surveyed, however, some sensors have been devised wherein the sensing elements actually contact the surface of the web. For example, in a caliper or thickness gauge used in the paper industry, a pair of opposed sensing elements contact opposite faces of the web. It has been found that such contacting sensors may be extremely difficult to maintain due to the build-up of pitch, dirt and the like on the surface of the sensing elements in contact with the web to the point where in some cases such sensors have been completely abandoned.

It will be apparent that for any of the devices where contact is made between the sensing device and the web, particularly in relation to a paper web, it is important that a permanent marking of the surface of the web does not occur. For this reason the stress concentrations that may be developed between the surface of the sensor element and the paper web must be controlled. This imposes limitations on the shape of contacting sensor element and the pressure of the sensor against the web. These limitations inherently imposed restrictions on the shape of the sensing contact that could be used in the thickness gauge described above.

The problems of dirt or resin build-up on a sensor element is extremely important if the contacting surface of the sensor is also required to have substantially optical contact properties. For example, in the equipment disclosed in U.S. application Ser. No. 683,477 now U.S. Pat. No. 4,092,068 entitled Surface Sensor filed May 6, 1976, inventors Lucas & Gracovetsky, optical sensors are disclosed wherein an optical window must contact the sheet being sensed. Major problems were encountered in initially attempting to design a window through which light could be projected onto the sheet and reflected back through the window to the detecting means while maintaining the accurate position of the detecting means relative to the surface. This requires that the window actually be in face to face relationship with the surface of the travelling web without damaging the web and remain clean for extended periods of use.

BRIEF DESCRIPTION OF THE INVENTION

The present invention describes a specific sensor window particularly adapted for the aparatus described in said co-pending application and provides a window that contacts the surface of the sheet of paper and is continuously maintained clean without marking of the sheet.

Broadly the present invention relates to a sensor element having a face adapted to contact the surface of a travelling sheet of paper, said face being a convex surface that is substantially in the form of a single base segment of a sphere having a radius of between 10 and 35 mm. Preferably this radius will be about 20 mm. The instantaneous area of contact between the surface and the face will have an area equivalent to a circle having a diameter of between 2 and 8 mm. In the preferred application of the present invention, the contacting element will be an optical window of appropriate hardness to resist abrasion and sufficiently transparent to permit the transmission of light from a light source therethrough onto the surface of the paper and reflected light back therethrough to a sensing element on the same side of the window as the light source.

Further features, objects and advantages will be evident from the following detailed description of the preferred embodiments of the present invention taken in conjunction with the accompanying drawings in which FIG. 1 is a partial section review through an optical sensor incorporating the present invention.

As shown in the illustrated arrangement the sensor 10 is composed of a main frame 12 which mounts a window mounting bracket 14 and a light projector 16. The light projector 16 includes an optical system mounted within the housing 18 that is axially positioned via the screw thread connections 20 to the mounting 16. A suitable light source may be connected to the element 18 by the threaded connection 22. Also mounted in the head 10 on the frame 12 are light channels 24 (only one shown) which direct reflected light to light detectors which are not shown.

Mounted on the mounting bracket 14 is the optical window 26 forming the subject of the present invention. This window 26 has its exposed surface 28 i.e. the surface contacting the web 30 in the form of a convex curve that is substantially a single base segment of a sphere the radius of which is indicated by the letter R and its based diameter by the letter r. Surprisingly it has been found that if the radius R does not exceed 35 mm and is not less than 10 mm an area of the window 26 is continuously maintained clean by contact with the relatively moving paper web and without marking the paper. In the preferred application, it has been found that by forming the surface 28 with a radius of 20 mm in the arrangement illustrated wherein r is equal to 12 mm an area having a diameter designated $r_2$ of about 2 mm is maintained clear throughout continual use of the sensor without marking the web.

The force with which the sensor 10 is pressed against the web 30 changes the operating characteristics of the window. It is important that the window deflects the papers slightly in an amount obtained in partially wrapping of the paper about the face 28 of the window. A minimum wrap of the paper web about the surface 28 requires that the area of contact between the web and the surface be equivalent to a circular area having a diameter of at least 2 mm i.e. thus the area of contact between the spherical surface 28 and the paper will result in a circle defined in the web at least 2 mm diameter. This area may not be a true circle depending on the tension in the web, shape of the sensor window and the longitudinal transverse forces generated in the web by the sensor window i.e. the area of contact between the window 28 and the web is determined in part by the web characteristics including the web tension. In any event the window must rub against and be in intimate contact with the surface 28 or likes for a distance in the machine (direction of paper movement) of at least 2 mm as described hereinabove and generally for not more than about 8 mm. Generally the area of contact will be substantially circular and will have a diameter in the range of 2 to 8 mm. The term substantially circular is intended to include off circular ellipses having their major dimension in the cross machine direction.

The area of contact determines the pressure (force per unit area) between the window and the paper—this pressure must be low, but the forces generated between the web and the window are not always accurately controlled. Thus for heavier grades of paper such as box board where high friction force is generated with little web deflection (i.e. pressures are more easily applied to the sensor) it is preferred to use a larger contact area and for the lighter weights a smaller contact area i.e. radius R preferably is larger for the heavier material. A radius of 20 mm is preferred for lighter grade papers such as offset papers but this radius also works well for heavier grades.

The shape of the surface 28 has been defined as "substantially in the form of a single base segment of a sphere" which is intended to clearly indicate that there are tolerances available and the surface may deviate from being "spherical", for example the curvature in a plane tranverse to the direction of web movement may be slightly different from curvature in a plane in the direction of web movement.

Modifications may be made without departing from the sphere of the intention as defined in the appended claims.

We claim:

1. In a sensor means, a sensor element having a face adapted to contact the surface of the travelling paper web, said face being a convex surface that is substantially in the form of a single base segment of the sphere having a radius of between 10 and 35 mm, said face contacting said surface of said web over an instantaneous area of contact having its dimension in the direction of travel of the paper of between 2 mm and 8 mm.

2. A sensor element as defined in claim 1 wherein said face forms the surface of an optical window through which light may be transmitted onto and reflected back through from said surface of said web.

3. A sensor element as defined in claim 2 wherein said radius is about 20 mm.

4. A sensor element is defined in claim 1 wherein said area of contact is substantially circular.

5. A sensor element as defined in claim 2 wherein said area of contact is substantially circular.

6. A sensor element as defined in claim 3 wherein said area of contact is substantially circular.

* * * * *